US008484010B2

(12) United States Patent
Tuszynski et al.

(10) Patent No.: US 8,484,010 B2
(45) Date of Patent: Jul. 9, 2013

(54) METHOD FOR DESIGNING AN APTAMER

(75) Inventors: Jack A. Tuszynski, Edmonton (CA);
Chih-Yuan Tseng, Edmonton (CA)

(73) Assignee: Technology Innovations, LLC, West Henrietta, NY (US)

( * ) Notice: Subject to any disclaimer, the term of this patent is extended or adjusted under 35 U.S.C. 154(b) by 0 days.

(21) Appl. No.: 13/298,830

(22) Filed: Nov. 17, 2011

(65) Prior Publication Data
US 2012/0123760 A1    May 17, 2012

Related U.S. Application Data

(60) Provisional application No. 61/458,063, filed on Nov. 17, 2010.

(51) Int. Cl.
G06G 7/48 (2006.01)
G06F 17/11 (2006.01)
G06F 17/50 (2006.01)

(52) U.S. Cl.
USPC .............................................. 703/19; 703/11

(58) Field of Classification Search
None
See application file for complete search history.

(56) References Cited

U.S. PATENT DOCUMENTS

| | | | |
|---|---|---|---|
| 5,325,091 | A | 6/1994 | Kaplan et al. |
| 5,450,598 | A | 9/1995 | Kaplan et al. |
| 5,625,554 | A | 4/1997 | Cutting et al. |
| 5,637,459 | A | 6/1997 | Burke et al. |
| 5,866,343 | A | 2/1999 | Blom et al. |
| 2004/0053310 | A1 * | 3/2004 | Shi et al. ............................ 435/6 |
| 2006/0257900 | A1 | 11/2006 | Hudson et al. |
| 2009/0094012 | A1 | 4/2009 | Clark |

OTHER PUBLICATIONS

Issur et al. Nucleic Acid Research, 2009, 37(11),3714-3722.*
Chushak et al Nucl. Acids Res., 37 (12), p. 1-9, doi: 10.1093/nar/gkp408, published online: May 21, 2009.*
Ewing et al. Journal of Computer-Aided Molecular Design, 15: 411-428, 2001.*
Brooijmans et al. Annu. Rev. Biophys. Biomol. Struct. 2003. 32:335-73.*
International Search Report in PCT/US2011/061176 dated Jul. 30, 2012.
NimJee, S. M., Rusconi, C. P., Sullenger, B. A. (2005) Aptamers: An emerging class of therapeutics, Annu. Rev. Med. 56: 555-583.
Hamula, C. L. A., Guthrie, J. W., Zhang, H., Li, X. F., Chris, Le X. (2006) Selection and analytical applications of aptamers, Trends in Anal. Chem. 25: 681-691.
James, W. (2000) Aptamer, In; Meyers, R. A., editor. Encyclopedia of Analytical Chemistry, Wiley, USA, p. 4848-4871.
James, W. (2007) Aptamers in the virologists' toolkit. J. of Gen. Viral. 88: 351-364.
Lao, Y.-H., Peck, K., Chen, L,-C. (2009) Enhancement of Aptamer Microarray Sensitivity through Spacer Optimization and Avidity Effect. Anal. Chem. 81: 1747-1754.
Levine, H. A., Nilsen-Hamilton, M. (2007) A mathematical analysis of SELEX. Comput. Biol. and Chem. 31: 11-35.

(Continued)

Primary Examiner — Michael Borin
(74) Attorney, Agent, or Firm — Hiscock & Barclay, LLP

(57) ABSTRACT

Disclosed in this specification is a method for identifying at least one aptamer that can bind to a bio-molecular target. The aptamer is designed in silico based on the structure of the target molecule. The process includes the steps of determining a first seed residue and growing an oligomer, one residue at a time, while maximizing the entropy of target-oligomer complex or minimizing the binding energy after the addition of each oligomer.

6 Claims, 9 Drawing Sheets

OTHER PUBLICATIONS

Kim, N., Gan, H. H., Schlick, T. (2007) A computational proposal for designing structured RNA pools for in vitro selection of RNAs. RNA 13: 478-492.

Kim, N., Shin, J. S., Elmetwaly, S., Gan, H. H., Schlick, T. (2007) RagPools: RNA-As Graph-Pools—a web server for assisting the design of structured RNA pools for in vitro selection. Bioinformatics 23: 2959-2960.

Chushak, Y., Stone, M. O. (2009) In silico selection of RNA aptamers. Nucl. Acids Res. 37: e87.

Jaynes, E. T. (1957) Information theory and statistical mechanics, Phys. Rev. 106: 620-630.

Jaynes, E. T. (1957) Information theory and statistical mechanics II. Phys. Rev. 108: 171-190.

Shore, J. E., Johnson, R. W. (1980) Axiomatic derivation of the principle of maximum entropy and the principle of minimum cross entropy. IEEE Trans. Inf. Theory IT-26: 26-37.

Shore, J, E., Johnson, R. W. (1981) Properties of cross-entropy minimization. IEEE Trans. Inf. Theory IT-27 472-482.

Caticha, A. (2004) Relative Entropy and Inductive Inference. In: Erickson, G., Zhal, Y., editors. Bayesian Inference and Maximum Entropy Methods in Science and Engineering. AIP Conf. Proc. 707, Melville, New York, USA, p. 75-96.

Caticha, A., Giffin, A. (2007), Updating Probabilities. In: Knuth, K. H., Catlcha, A., Center, J. L., Giffin, A., Rodriguez, C. C., editors. Bayesian Inference and Maximum Entropy Methods in Science and Engineering, AIP Conf. Proc. 954, Melville, New York, USA, p. 74-84.

Tseng, C,-Y., Catlcha, A. (2008) Using Relative Entropy to Find Optimal Approximations: an Application to Simple Fluids, Physica A 387: 6759-6770.

Tseng, C.-Y. (2006) Entropic Criterion for Model Selection. Physica A 370: 530-538.

Chen, C,-C., Tseng, C.-Y., Dong, J.-J. (2007) New entropy-based method for variables selection and its application to the debris-flow hazard assessment, Eng. Geo. 94: 19-24.

Paborsky, L. R., McCurdy, S. N., Griffin, L. C., Toole, J. J., Leung, L. L. K. (1993) The single-stranded DNA aptamer-binding site of human thrombin. J. Biol. Chem. 268: 20808-20811.

Padmanabhan, K., Padmanabhan, K. P., Ferrara, J, D., Sadler, J. E., Tulinsky, A. (1993) The structure of a-thrombin inhibited by a 15-mer single-stranded DNA aptamer, J. Biol. Chem. 268: 17651-17654.

Montaville, P., Neumann, J, M., Russo-Marie, F., Ochsenbein, F. (2002) A new consensus sequence for phosphatidylserine recognition by annexins. J. Biol. Chem. 277: 24684-24693.

Schaftenaar, G., Noordik, J. (2000) Moiden: A pre- and post-processing program for molecular and electronic structures. J. Comput.-Aided Mol. Des. 14: 123-134.

Schmidt, M. W., Baldridge, K. K., Boatz, J. A., Elbert, S. T., Gordon, M. S., Jensen, J. H., Koseki, S., Matsunaga, N., Nguyen, K. A., Su, S., Windus, T. L., Dupuis, M., Montgomery, J. A. (1993) General atomic and molecular electronic structure system. J. Comput. Chem. 14: 1347-1363.

Dewar, M., Dieter, K. (1986) Evaluation of AM1 calculated proton affinities and deprotonation enthalpies. J. Am. Chem. Soc. 108: 8075-8086.

Dewar, M., Zoebisch, E., Healy, E., Stewart, J. (1985) AM1: A new general purpose quantum mechanical molecular model. J. Am. Chem. Soc. 107: 3902-3909.

Luscombe, N. M., Laskowski, R. A., Thornton, J. M. (1997) NUCPLOT: a program to generate schematic diagams of protein-DNA Interactions. Nucl. Acids Res. 25: 4940-4945.

Reyes, C., Koliman, P. (2000) Structure and thermodynamics of RNA-protein binding: Using molecular dynamics and free energy analyses to calculate the free energies of binding and conformational change. J. Mol. Biol. 297: 1145-1158.

Lee, M. R., Duan, Y., Kollman, P. A. (2000) Use of MM-PB/SA in estimating the free energies of proteins: Application to native, intermediates, and unfolded vilin headpiece. Proteins 39: 309-316.

van Dijk, M., Bonvin, A. M. J. J. (2009) 3D-DART: a DNA structure modelling server. Nucl. Acids Res. 37: W235-W239.

Humphrey, W., Dalke, A., Schulten, K. (1996) VMD—Visual molecular dynamics. J Mol. Graph. 14: 33-38.

Bock, L. C., Griffin, L. C., Latham, J. A., Vermass, E. H., Toole, J. J. (1992) Selection of single-stranded DNA molecules that bind and Inhibit human thrombin. Nature 355: 584-566.

Tasset, D. M., Kubik, M. F., Steiner, W. (1997) Oligonucleotide inhibitors of human thrombin that bind distinct epitopes. J. Mol. Biol. 272: 688-698.

Macaya, R. F., Schultze, P., Smith, F. W., Roe, J. A., Feigon, J. (1993) Thrombin-binding DNA aptamer forms a unimolecular quadruplex structure in solution. Proc. Natl. Acad. Sci. USA 90: 3745-3749.

Kankla, B. I., Marky, L. A. (2001) Folding of the thrombin aptamer into a G-quadruplex with Sr2+ stability, heat, and hydration. J. Am. Chem. Soc. 123: 10799-10804.

Tseng, C.-Y., Ashrafuzzaman, M. Mane, J. Y., Kapty, J., Mercer, J. R. and Tuszynskl, J. A. (2011) Entropic fragment based approach to aptamer design. Chem Biol & Drug Design 78, 1.

\* cited by examiner

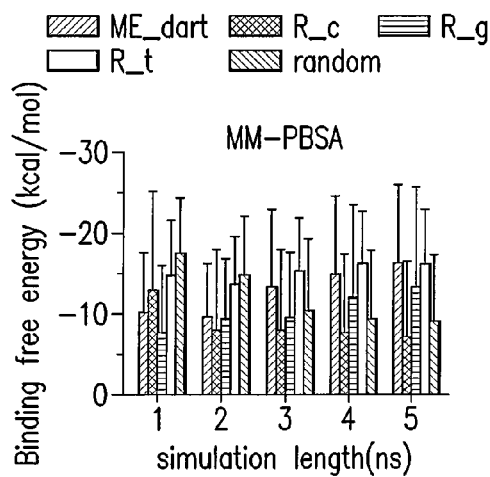
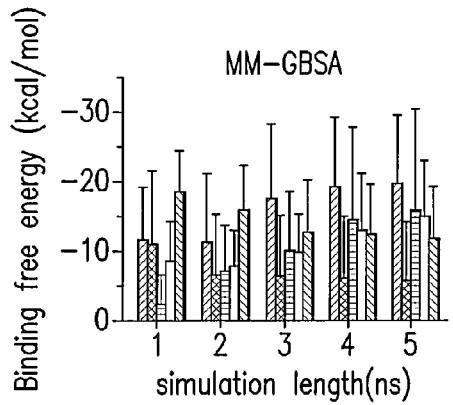
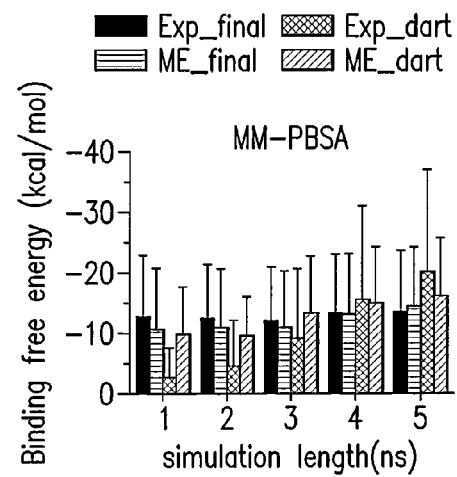
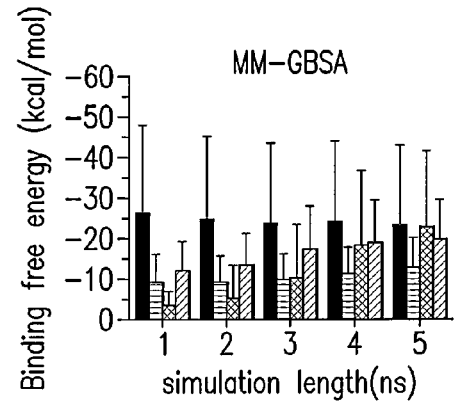
FIG. 7A
FIG. 7B

METHOD FOR DESIGNING AN APTAMER

CROSS-REFERENCE TO RELATED APPLICATIONS

This application claims priority to and the benefit of U.S. provisional patent application Ser. No. 61/458,063, filed Nov. 17, 2010, which application is incorporated herein by reference in its entirety.

FIELD OF THE INVENTION

This invention relates, in one embodiment, to a computer modeling method for determining an aptamer sequence that will bind to a particular target molecule.

BACKGROUND

Aptamers are small, single stranded biomolecules, typically oligonucleotides (either DNA or RNA) or peptides, that bind to a specific target molecule (e.g. a protein or small molecule such as a steroid). They can be considered analogous to antibodies in their specificity but, unlike antibodies, aptamers are relatively small molecules. Peptide-based aptamers are generally less than thirty residues long while nucleotide-based aptamers are typically less than one hundred residues long.

Conventionally, aptamers are discovered using the SELEX process (Systematic Evoluatoin of Legands by Exponential Enrichment). See U.S. Pat. No. 5,637,459 (Burke). In this process, a large olignocleotide library ($10^{14}$ to $10^{15}$ different sequences) of random sequences is exposed to the target molecule. Those sequences that do not bond to the target are removed. Those sequences that do bond are eluted and subjected to polymerase chain reaction (PRC). This process can be repeated multiple times until the tightest bonding sequence is isolated.

The SELEX process is somewhat limited. In certain occasions, a target is located that fails to tightly bond to any aptamer in the library of random sequences. The process is also time consuming. Depending on the particular application, this can require anywhere from a few days to a few months to complete. Additionally, isolated aptamers will often need to be re-engineered to reduce their sequence length and impart additional favorable biological properties. It would be desirable to find other methods for determining an aptamer sequence that do not suffer from at least some of this shortcomings.

Some virtual screening approaches to aptamer selection have been contemplated. See, for example: Chushak Y and Stone M O Nucl. Acids Res. 37 (2009) e87; Kim Bioinformatics 23: 2959-2960; Kim RNA 13: 478-492; Kevine Comput. Biol. and Chem. 31: 11-35. Over the past several years, various research groups have attempted to develop theoretical methods in order to speed up the SELEX process and design optimal aptamer sequences. Despite theoretical modeling of the working principle involved in SELEX process, various in silico approaches are favored by several groups. There are two general directions—a focus on developing a computational design of structured random pools such as RagPools and application of a virtual screening process.

Yet both directions possess some disadvantages. The first one is hindered by the requirement of a library of reasonably good starting sequences. It also requires prediction tools to arrive at candidate structures and the associated structural distributions. While this direction provides optimal choices for the design of a random pool for SELEX-prepared structures, in the final aptamer selection one still needs to go through the SELEX process in order to identify the "right" aptamer. The second direction requires information about the binding interfaces, "good" prediction of the tertiary structures of nucleotide sequences, and the availability of immense computational resources. One has to screen at most $4^N$ N-mer RNA/DNA sequences to be able to analyze sequence diversity and structural complexity. The required computational power would be prohibitively large to complete the screening process. Another challenge involves the prediction of tertiary structures for arbitrary RNA/DNA sequences. Although the development of the RNA/DNA 2D and 3D structural prediction methods is promising, their validation is still questionable.

SUMMARY OF THE INVENTION

The invention comprises, in one form thereof, a method for designing an aptamer that binds to a target biomolecule. Given the structural information of the target, the preferred probability distribution of having an aptamer that is most likely to interact with the target is determined using a seed-and-grow approach. The aptamer is computationally grown, one residue at a time, until insignificant increases in binding efficiency result. In another embodiment, the method provides a list of aptamers and ranks each aptamer in terms of entropy value of the target molecule-aptamer complex.

BRIEF DESCRIPTION OF THE DRAWINGS

The present invention is disclosed with reference to the accompanying drawings, wherein:

FIG. 7A and FIG. 7B show the binding free energies of five different aptamer analogs (FIG. 7A) and four different initial confirmations (FIG. 7B);

Corresponding reference characters indicate corresponding parts throughout the several views. The examples set out herein illustrate several embodiments of the invention but should not be construed as limiting the scope of the invention in any manner.

DETAILED DESCRIPTION

Figure 1:
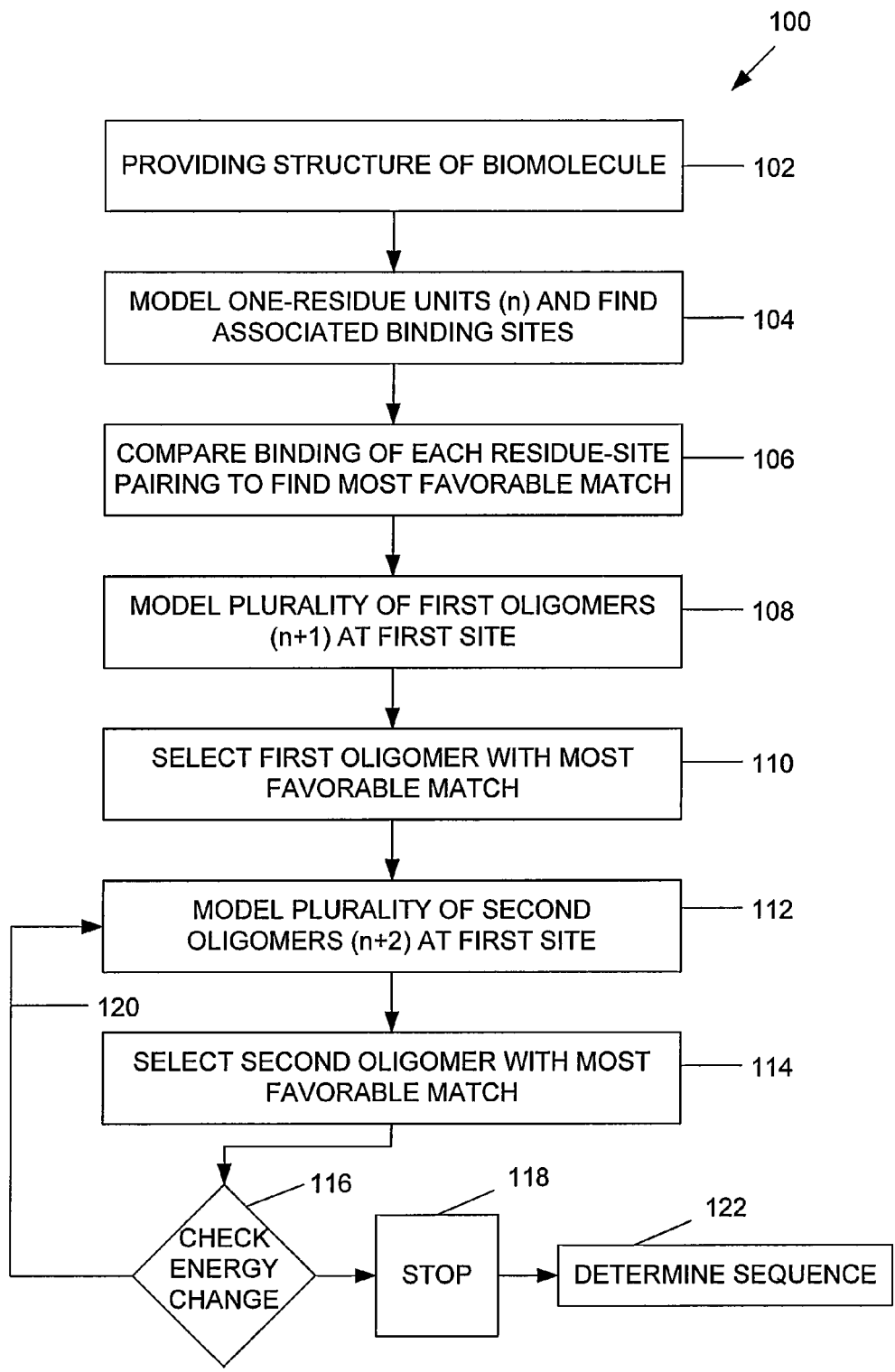
FIG. 1 is a flow diagram of one process of the invention.

Referring to FIG. 1, method 100 detects the steps involved in a "seed-and-grow" approach to aptamer design. Method 100 begins with step 102 in which the structure of a particular biomolecular target is provided to a computer. For example, the tertiary or quaternary structure of a particular protein may be provided to a computer. Alternatively, the primary structure of a protein may be provided and the higher order structure is thereafter determined using molecular modeling techniques. Other biomolecular targets include small molecules, such as phospholipids, membrane-bound proteins, other cellular surface receptors, and the like.

In step 104, once the target structure has been provided to the computer, modeling experiments are conducted to determine the binding site of a plurality of single residues. For example, the single residues may be nucleotides (either DNA or RNA nucleotides) where there are only four possibilities. In such a nucleotide-based embodiment, four modeling experiments are conducted to determine the most favorable binding site for A, G, C and T, respectively. Each of these computer models also provides a quantitative evaluation of the entropy of each residue to its particular binding site.

Figure 2:
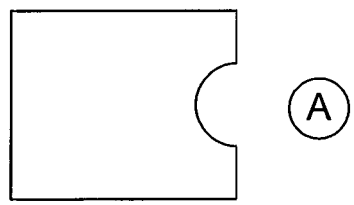
FIG. 2 is a depiction of the probability distributions of four one-residue potential aptamers binding to a given binding site.
Figure 2:
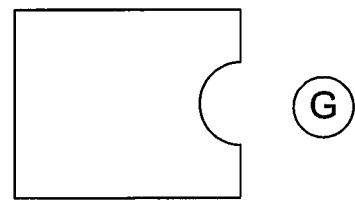
Figure 2:
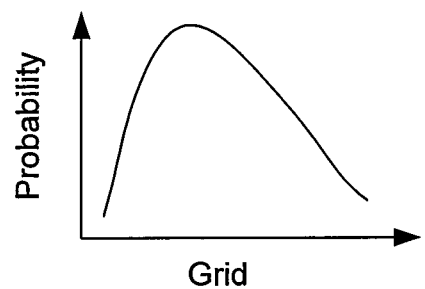
Figure 2:
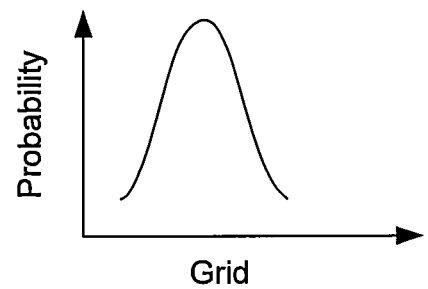
Figure 2:
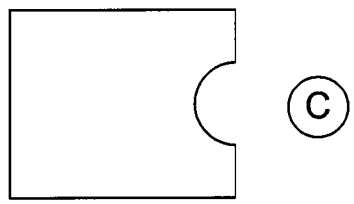
Figure 2:
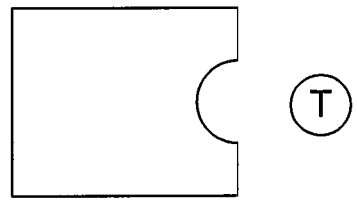
Figure 2:
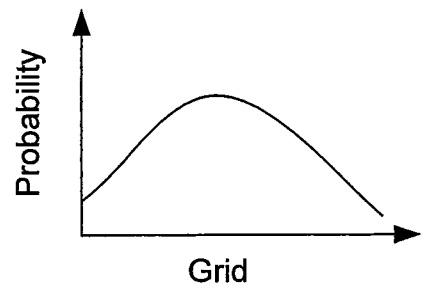
Figure 2:
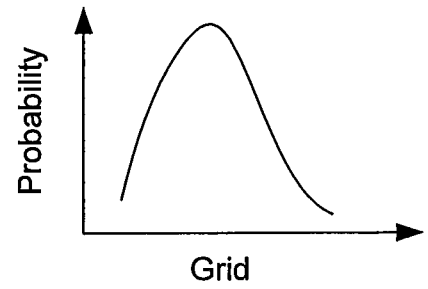

In step 106, the entropy of each single residue-site pairing is compared to the other three modeled residue-site pairs and the most favorable residue-site pairing is determined. In the aforementioned nucleotide-based example, four nucleotide-site pairs are modeled. See FIG. 2. The entropies of these four nucleotide-binding sites are compared to one another and it was determined that the most favorable pairing is nucleotide A at a particular first binding site.

Figure 3:
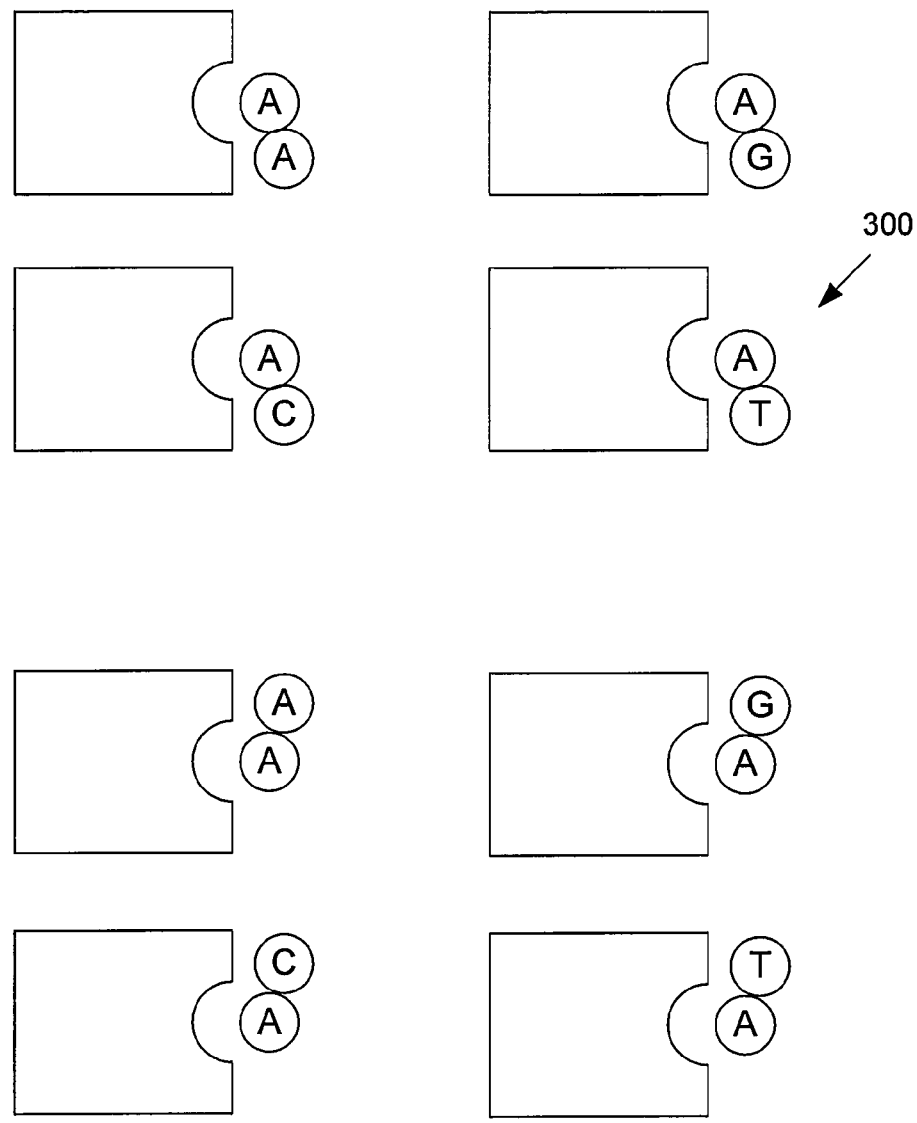
FIG. 3 is a depiction of eight two-residue aptamers binding to a binding site.

In step 108, a plurality of two-residue oligomers are modeled using the residue-site pairing identified in step 106 as a starting point. The two-residue oligomer includes the residue identified in step 106 and is modeled at the same first binding site. The two-residue oligomer further includes a second residue. In the aforementioned example, DNA nucleotides were being modeled and it was determined nucleotide A bonded to a particular first binding site. As shown in FIG. 3, eight models are conducted that add four possible nucleotides to the 3' side of A and four possible nucleotides to the 5' side of A. In certain situations it is possible to model less than eight possibilities. For example, if the binding site becomes so congested that another residue cannot be added at the 5' terminus, then half of the possibilities can be omitted.

In step 110, the oligomer with the maximum entropy, as determined in step 108, is selected. Referring to the hypothetical example shown in FIG. 3, it was found that oligomer 300 had the maximum entropy of the eight models. Since models have already been generated for the non-selected oligomers, the entropy can be used to rank the oligomers. In one such embodiment, the non-selected oligomers are also subjected to the remainder of the steps in the process. In such an embodiment, a series of aptamers results, rank ordered by the entropy of the target-aptamer complexes.

Figure 4:
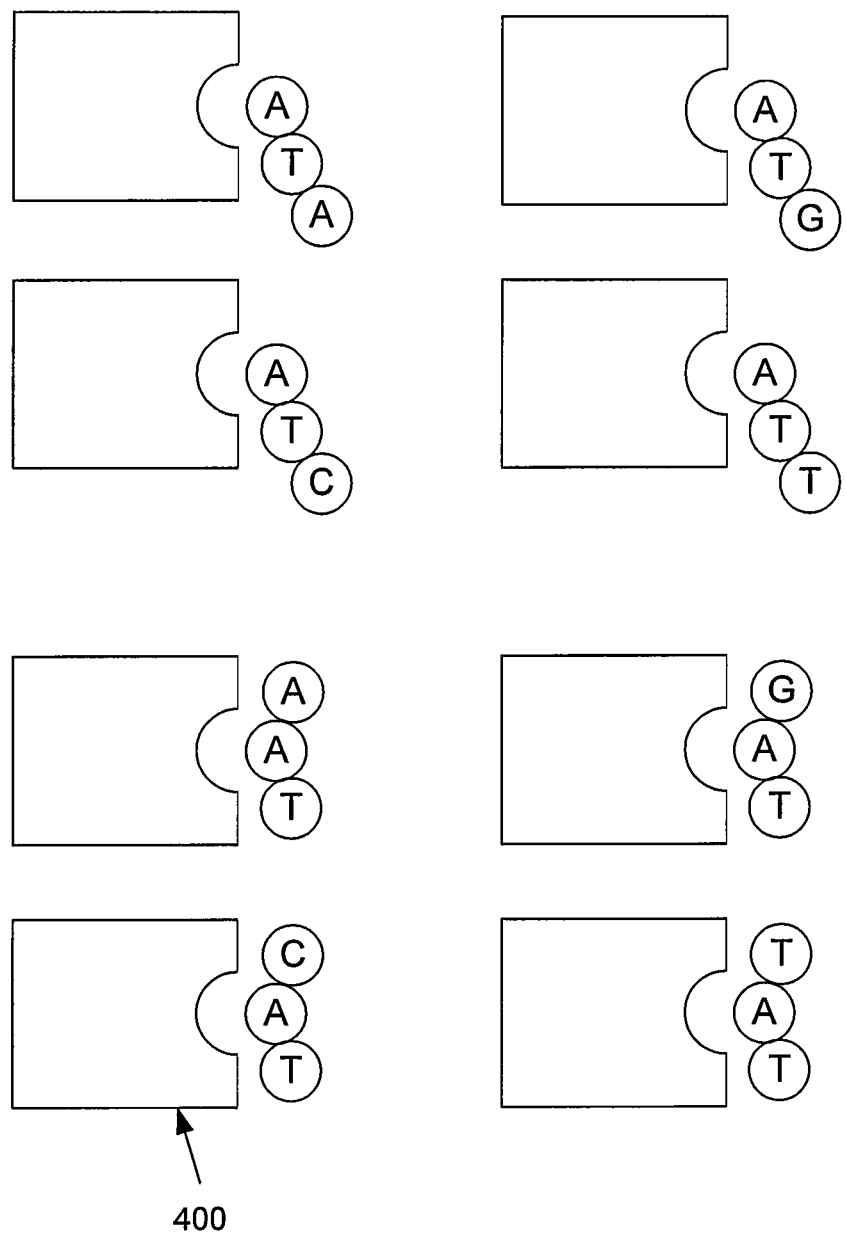
FIG. 4 is a depiction of eight three-residue aptamers binding to a binding site.

In step 112, a plurality of three-residue long oligomers are modeled using the oligomer identified in step 110 as a starting point. These oligomers are once again modeled at the same first binding site identified in step 106. As shown in FIG. 4, eight models are conducted that add four possible nucleotides to the 3' side of the AT oligonucleotide identified in step 110 and four possible nucleotides to the 5' side of the same sequence.

In step 114, the three-residue long oligomer with the maximum entropy, as determined in step 112, is selected. Referring to the hypothetical example shown in FIG. 4, it was found that oligomer 400 had the maximum entropy of the eight models.

In step 116, the change in entropy that was due to the addition of the last residue is analyzed. The entropy of the two-residue oligomer is compared to that of the three-residue oligomer. The difference in entropy is the contribution of the third residue. If there is less than a predetermined improvement in entropy due to the addition of the most recent residue, then the sequence is deemed sufficiently optimized and the process is stopped (step 118). Alternatively, if the improvement in entropy exceeds the predetermined threshold then the sequence is deemed to not be optimized. Step 120 is then executed wherein another residue is added to the oligomer (now a four-residue oligomer) and eight modeling experiments are conducted in a manner analogous to steps 112 and 114. In one embodiment, step 120 is repeated until less than a 20% increase in entropy is found. In another embodiment, step 120 is repeated until less than a 10% increase in entropy is found. In yet another embodiment, a different threshold is set. In other embodiments, the increases in entropy are monitored over multiple residues. For example, the entropy of the 6 mer oligomer is compared to the entropies of the 7 mer, 8 mer, and 9 mer. The process is halted when the lasting n-mer additions fail to increase the entropies over a threshold amount.

In step 122 the final aptamer sequence is determined. The final aptamer sequence may be either the complete sequence of N residues (which includes the residue that resulted in only minimal improvement in entropy) or be the sequence of N−1 residues (which omits the residue that provided only minimal improvement).

A variety of residues can be selected, thereby producing a variety of aptamers. For example, the residues may be the DNA nucleotides (A, T, G and C—adenine, thymine, guanine and cytosine, respectively). Alternatively, RNA nucleotides (A, U, C and G—adenine, uracil, guanine and cytosine, respectively) may also be used. Single residues may also include single amino acids such as the twenty-one well known amino acids found in eukaryotic cells.

The inventive method provides a promising initial set of templates for aptamer design and does so based solely on the structure of the biomolecular target. Subsequently, these templates can be engineered, either computationally or experimentally, for further optimization regarding their binding affinity without going through any SELEX processes.

The aptamers identified by the inventive method have a myriad of applications. Due to their specificity, they have potent molecular recognition properties rivaling those of antibodies. This permits them to both alter the biological properties of the molecule to which they bind as well as function as a detector or identify the presence and concentration of the target molecule. Due to their small size, they typically undergo relatively rapid biodegradation. Advantageously, this permits them to be used as biosensors as well as permits them to be rapidly cleared from the bloodstream.

A number of method can be used to optimize the above mentioned process. One method is the maximum entropy (ME) method. This permits the assignment of probability distributions based on a limited amount of information denoted by MaxEnt. (Jaynes, E. T. (1957) Phys. Rev. 106: 620-630 and Jaynes, E. T. (1957) Phys. Rev. 108: 171-190). One also needs a method of updating probability distributions from a priori when new information becomes available denoted by MEU (Maximum Entropy Updating). See Shore, J. E., Johnson, R. W. (1980); IEEE Trans. Inf. Theory IT-26: 26-37 Shore, J. E., Johnson, R. W. (1981) IEEE Trans. Inf. Theory IT-27 472-482; Caticha, A. (2004) Science and Engineering. AIP Conf. Proc. 707, Melville, N.Y., USA, p. 75-96; Caticha, A., Giffin, A. (2007). In: Knuth, K. H., Caticha, A., Center, J. L., Giffin, A., Rodríguez, C. C., editors. AIP Conf. Proc. 954, Melville, N.Y., USA, p. 74-84. Additionally a selection criterion for different probability distributions associated with various types of nucleotides is also needed. Tseng, C.-Y., Caticha, A. (2008) Physica A 387: 6759-6770; Tseng, C.-Y. (2006) Physica A 370: 530-538; Chen, C.-C., Tseng, C.-Y., Dong, J.-J. (2007) Eng. Geo. 94: 19-24.

Steps 102 and 104, when performed using the MaxEnt method aim to determine the probability distribution of a preferred first nucleotide (nt1) seed that is most likely to interact with targets (tar). Note that, in the present example, nucleotides denoted by "nt" can be nucleotide A (adenine), C (cytosine), G (guanine), or T/U (thymine/uracil). Here, the Hamiltonian of the complex of the target "tar" and the first single nucleotide "nt1" as the input information is given by $$H_{Total}(Q_{\{i\}}, q_{\{j\}}^1) = H_{tar}(Q_{\{i\}}) + H_{nt1}(q_{\{j\}}^1) + H_{tar-nt1}(Q_{\{i\}}, q_{\{j\}}^1) + H_{solvent}, \quad (1)$$

where $Q_{\{i\}} = \{\vec{R}_{\{i\}}, \vec{P}_{\{i\}}\}$ stands for $\{i=1, \ldots, N_Q\}$ atomic spatial coordinates and momenta of the $N_Q$-atom target and $q_{\{j\}}^1 = \{\vec{r}_{\{j\}}^1, \vec{p}_{\{j\}}^1\}$ for the $\{j=1, \ldots, N_{nt1}\}$ atomic spatial coordinates and momenta of the first $N_{nt1}$-atom nucleotide. Furthermore, $H_{tar}(Q_{\{i\}})$ is the total internal energy of the target "tar", $H_{nt1}(q_{\{j\}}^1)$ is the total internal energy of the first nucleotide "nt1", $H_{tar-nt1}(Q_{\{i\}}, q_{\{j\}}^1)$ denotes the interaction energy of the target and the first nucleotide and $H_{solvent}$ represents the solvation energy. The MaxEnt is then utilized to determine the preferred probability distribution of the first nucleotide nt1 in state $q_{\{j\}}^1$ interacting with the target tar in state $Q_{\{i\}}$, which is given by $$P_{nt1}(Q_{\{i\}}, q_{\{j\}}^1) = \frac{1}{Z_{nt}^1} e^{-\beta H_{Total}(Q_{\{i\}}, q_{\{j\}}^1)}, \quad (2)$$

where $$z_{nt1}^1 = \sum_{i=1}^{N_Q} \sum_{j=1}^{N_{nt1}} \int dQ_i dq_j^1 e^{-\beta H_{Total}(Q_{\{i\}}, q_{\{j\}}^1)}.$$

Therefore, one can determine the probability distributions of all four nucleotides at specific locations and orientations that interact independently with the target protein. Next, the entropic criterion is utilized to rank the four probability distributions based on relative entropy $$S[P_{nt1}|P_{ref}] = -\sum_{i=1}^{N_Q} \sum_{j=1}^{N_{nt1}} \int dQ_i dq_j^1 P_{nt1}(Q_{\{i\}}, q_{\{j\}}^1) \log \frac{P_{nt1}(Q_{\{i\}}, q_{\{j\}}^1)}{P_{ref}(Q_{\{i\}}, q_{\{j\}}^1)}, \quad (3)$$

where $P_{ref}(Q_{\{i\}}, q_{\{j\}}^1)$ denotes a reference distribution. Therefore, the maximum $S[P_{nt1}|P_{ref}]$ indicates that $P_{nt1}(Q_{\{i\}}, q_{\{j\}}^1)$ is equivalent to a uniform distribution and contains no information about the interactions. Namely, it suggests that there is no interaction between the nucleotide and the target protein. This relative entropy then gives a ranking scheme of four types of nucleotides that interact with the target. The preferred type of the first nucleotide is considered to interact most strongly with the target and leads to the minimum relative entropy.

Steps 108 and 110 determine the probability distribution of preferred nucleotides that will connect to the previous nucleotide given the results from the previous step as the prior distribution. The same strategy used previously is applied again. However, because this step takes the results from the previous step into account, the MEU, a tool for updating information, rather than the MaxEnt is used. When the new information, the total energy of the target in state $Q_{\{i\}}$ and two concatenated nucleotides in states $q_{\{k\}}^2$ and $q_{\{j\}}^1$, respectively, $H_{total}(Q_{\{i\}}, q_{\{k\}}^2, q_{\{j\}}^1)$, is obtained, the posterior probability distribution updated from the prior distribution $P_{nt1}(Q_{\{i\}}, q_{\{j\}}^1)$ is given by $$P_{nt}(Q_{\{i\}}, q_{\{k\}}^2, q_{\{j\}}^1) = P_{nt1}(Q_{\{i\}}, q_{\{j\}}^1) \frac{e^{-\beta H_{Total}(Q_{\{i\}}, q_{\{k\}}^2, q_{\{j\}}^1)}}{Z_{nt}^2}, \quad (4)$$

where $$Z_{nt}^2 = \sum_{i=1}^{N_Q} \sum_{j=1}^{N_{nt1}} \sum_{k=1}^{N_{nt2}} \int dQ_i dq_j^1 dq_k^2 P_{nt1}(Q_{\{i\}}, q_{\{j\}}^1) \exp(-\beta H_{Total}(Q_{\{i\}}, q_{\{k\}}^2, q_{\{j\}}^1)).$$

Again, the probability distribution of a preferred dimer can be determined by the preference $S[P_{nt}(Q_{\{i\}}, q_{\{k\}}^2, q_{\{j\}}^1) | P_{ref}]$ of sixteen possibilities involved. The resulting dimer is then used as the prior distribution for determining the third nucleotide (steps 112 and 114). By repeating (step 120) the same procedure, one can obtain the joint probability distribution of an L-mer nucleotide sequence given by $$P_{nt}(Q_{\{i\}}, q_{\{k\}}^L, \ldots, q_{\{j\}}^1) = \quad (5)$$
$$P_{nt}(Q_{\{i\}}, q_{\{k'\}}^{L-1}, \ldots, q_{\{j\}}^1) \frac{e^{-\beta H_{Total}(Q_{\{i\}}, q_{\{k\}}^L, \ldots, q_{\{j\}}^1)}}{Z_{nt}^L},$$

where $H_{Total}(Q_{\{i\}}, q_{\{k\}}^L, \ldots, q_{\{j\}}^1)$ is the total energy of the target at state $Q_{\{i\}}$ and the L-mer nucleotide sequence and the partition function is $$Z_{nt}^L = \sum_{i=1}^{N_Q} \sum_{j=1}^{N_{nt1}} \cdots \sum_{k=1}^{N_{ntL}} \int dQ_i \prod_{m=1, \alpha=\{j,\ldots,k\}}^{L} dq_\alpha^m P_{nt}(Q_{\{i\}}, q_{\{k'\}}^{L-1}, \ldots, q_{\{j\}}^1) \quad (6)$$
$$\exp(-\beta H_{Total}(Q_{\{i\}}, q_{\{k\}}^L, q_{\{k'\}}^{L-1} \ldots, q_{\{j\}}^1)).$$

Finally, the probability distribution of the preferred L-mer sequence is determined by the preference $S[P_{nt}(Q_{\{i\}}, q_{\{k\}}^L, \ldots, q_{\{j\}}^1) | P_{ref}]$ of all possible combinations. To determine the preferred length L, the entropic criterion was again used. When the relative entropy of the target-nucleotide fragment complex in the growth process is saturated, it indicates that the effect of the corresponding nucleotide on the interactions of the complex is at a global minimum. Namely, the portion grown in the ME aptamer after the saturation step does not play an important role in the interactions and the preferred length L is the number of nucleotides grown before the saturation step.

In practice, the partition functions of each step were calculated in a discrete space rather than in a continuous space, with $dQ_{\{i\}}$ and $dq_{\{\alpha\}}^m$, as shown in the above equations to determine the probability distributions. Two types of grid spaces were generated for this purpose. In the first step, a cubic grid space surrounding the targets of interest is created. Each grid point represents a possible location and a possible orientation for first nucleotide. Afterward, an orientation grid space is generated to account for the possible orientations of the nucleotide with respect to the previous one. Namely, both methods will properly sample the nucleotide conformational space. More details of this sampling approach are summarized in Supporting Information of Tseng, C.-Y., Ashrafuzzaman, M, Mane, J. Y., Kapty, J., Mercer, J. R. and Tuszynski, J. A. (2011) Entropic fragment based approach to aptamer design. Chem Biol & Drug Design 78, 1.

Theoretically, the maximum $P_{nt}(Q_{\{i\}}, q_{\{k\}}^L, \ldots, q_{\{j\}}^1)$ of an L-mer sequence at specific locations and orientations corresponds to the global entropy maximum and is preferred over all other possibilities. However, it will require expensive computational resources to compute all joint probability distributions to finally determine such an L-mer sequence. For example, suppose there are $Ng_i$ grid points to be calculated at the $i^{th}$ step of the growth process. To compute the energy of a total of $$4^L \prod_{i=1}^{L} Ng_i$$

grid points for the L-mer sequence. Instead, consider only an approximation of the prior probability distribution at each step, $P_{nt}(Q_{\{i\}}, \hat{q}_{\{k\}}^{L-1}) = P_{nt}(Q_{\{i\}}, q_{\{k\}}^{L-1}) \delta(q_{\{k\}}^{L-1} - \hat{q}_{\{k\}}^{L-1})$, where $\hat{q}_{\{k\}}^{L-1}$ is the state, in which an (L–1)-mer sequence has the maximum probability of interacting with the target. Although exact probability distributions were not taken into account, the final L-mer sequence obtained based on the approximated priors is still highly likely to interact with the target. Because entropy is an extensive quantity, the total entropy of an L-mer aptamer is the sum of the entropies obtained for all L nucleotides. The preferred state of a nucleotide selected in each step is approximately at the maximum entropy state. Therefore, the sum of all maximum entropies at each step gives the total entropy that is close to the global maximum value. On the other hand, the determined L-mer aptamer will likely be preferred over all other sequences. However, because the Entropic Fragment Based Approach (EFBA) actually provides a ranking scheme of all possible sequences, there is no requirement to select a single sequence. A set of top candidate aptamers, ME aptamers, will be considered either for a further in silico or an experimental validation.

The "seed-and-grow" approach described in this specification provides a substantial reduction in the amount of time required to identify a target aptamer sequence compared to the conventional SELEX approach. If approximately 150 k grids are used, the computational time required to determine the first seed residue is approximately 1 day if 150 CPUs are used and the residues are nucleotides. The next nucleotide can be determined in about 1 additional hour if 80 CPUs are used (10 k grids). Entire aptamer sequences can be designed in well under one week. This can be done even when other techniques, such as SELEX, fails to provide any experimentally determined aptamers.

In certain instances, certain data management techniques are also applicable to the computations of the instant invention. It is it contemplated to utilize the so-called Finite State Machines (FSM) and Fine State Transducers (FST) to increase the speed of computations performed in conjunction with the invention. Reference may be had to U.S. Pat. No. 5,325,091 (Kaplan); U.S. Pat. No. 5,450,598 (Kaplan) and U.S. Pat. No. 5,625,554 (Cutting). The content of the aforementioned patents is hereby incorporated by reference into this specification.

EXPERIMENTAL

Two types of molecular targets were considered to illustrate the applicability of the EFBA in concrete cases.

First, to illustrate the designing process, thrombin was chosen as the first target. Thrombin is a 37 KDa coagulation protein (PDB ID: 1HUT) and was selected since there are confirmed binding sites and a known aptamer had previously been determined through SELEX. The crystal structure of thrombin was equilibrated for 1 ns using molecular dynamics (MD) simulations under explicit water using the TIP3P model. (step 102) An aptamer primary structure was determined as described below.

Thereafter, in silico experiments were performed to assess the binding affinity and selectivity of the prediction and control results. Two quantities, hydrogen bond interactions and binding free energy, were considered in our analysis. For the hydrogen bond interaction analysis, the algorithm NUCPLOT was used to identify hydrogen bond and non-bonded interactions and to visualize the interactions in two dimensions. For binding free energy estimation, the MM-PBSA/GBSA package from Amber 10 was utilized. For both analyses, the structural data were collected from MD simulations with five various simulation lengths: 1, 2, 3, 4 and 5 ns, respectively.

Second, the phospholipid PS was chosen as a second target because of its important role in cell membrane transformation during apoptosis. The molecular model of PS was manually constructed using the MOLDEN program. The resulting structure was then minimized with the GAMESS-US program using the AM1 semi-empirical method. (step 102) Similar to the thrombin case, the PS structure was further equilibrated for 1 ns for aptamer design. Furthermore, the molecular model of phosphatidylcholine (PC) was also created using the same method for computationally investigating the binding selectivity of ME aptamers.

Two of the top-ranked 6-mer DNA designed aptamers targeting PS were chosen for experimental investigations. Both sequences containing fluorescence tags (6FAM is on the 3' end of the DNA sequence) were obtained from Integrated DNA Technologies, Commercial Park, Coralville Iowa, USA. 96 well assay plates for fluorescence assays using FLUOstar OPTIMA (BMG Labtech GmbH, Offenburg, Germany) were from Corning Inc., New York, USA. Two lipids, 1,2-dipalmitoyl-sn-glycero-3-phosphatidylcholine (DPPC) and 1,2-dipalmitoyl-sn-glycero-3-phospho-L-serine (sodium salt) (DPPS) in chloroform stock and cholesterol (powder) were obtained from Avanti Polar Lipids (Alabaster, Ala., USA). They were used without further purification.

The software package Amber 10 was applied for energy calculations in the design process. Before the EFBA was initiated, the targets and the four fragment nucleotides were energy minimized using the steepest descent method for the first ten cycles and then followed by a conjugate gradient for another 1000 cycles at 300K in Amber 10. Subsequently, the total energy of the complex composed of the target and fragments at specific grid points was calculated using an implicit water model. The potential cutoff distance was set to 12 Å. Based on the grid space created in Supporting Information of Tseng, C.-Y., Ashrafuzzaman, M, Mane, J. Y., Kapty, J., Mercer, J. R. and Tuszynski, J. A. (2011) Entropic fragment based approach to aptamer design. Chem Biol & Drug Design 78, 1, it takes between two and three hours of computation time to determine one preferred nucleotide using a cluster consisting of 72 CPUs.

Amber 10 was also used for MD simulations to equilibrate the final structure determined for the in silico binding affinity and selectivity analysis. During the equilibration of the complex using the explicit water TIP3P model, Langevin dynamics were first applied to heat up the system for 200 ps with targets being restrained using a harmonic potential (force constant k=100 N/m) to obtain its energy minimized structure. Pressure regulation was then introduced in the simulation to equilibrate solvent density for another 200 ps in addition to temperature regulation. The MD production run then continued for 5 ns. Note that the targets were gently restrained with a harmonic potential with a force constant k=10 N/m to the structure of thrombin and to the tail including phosphorus in PS and PC during the production MD runs.

Example 1

Thrombin Aptamer—Determination of Predicted Aptamer

Figure 5:
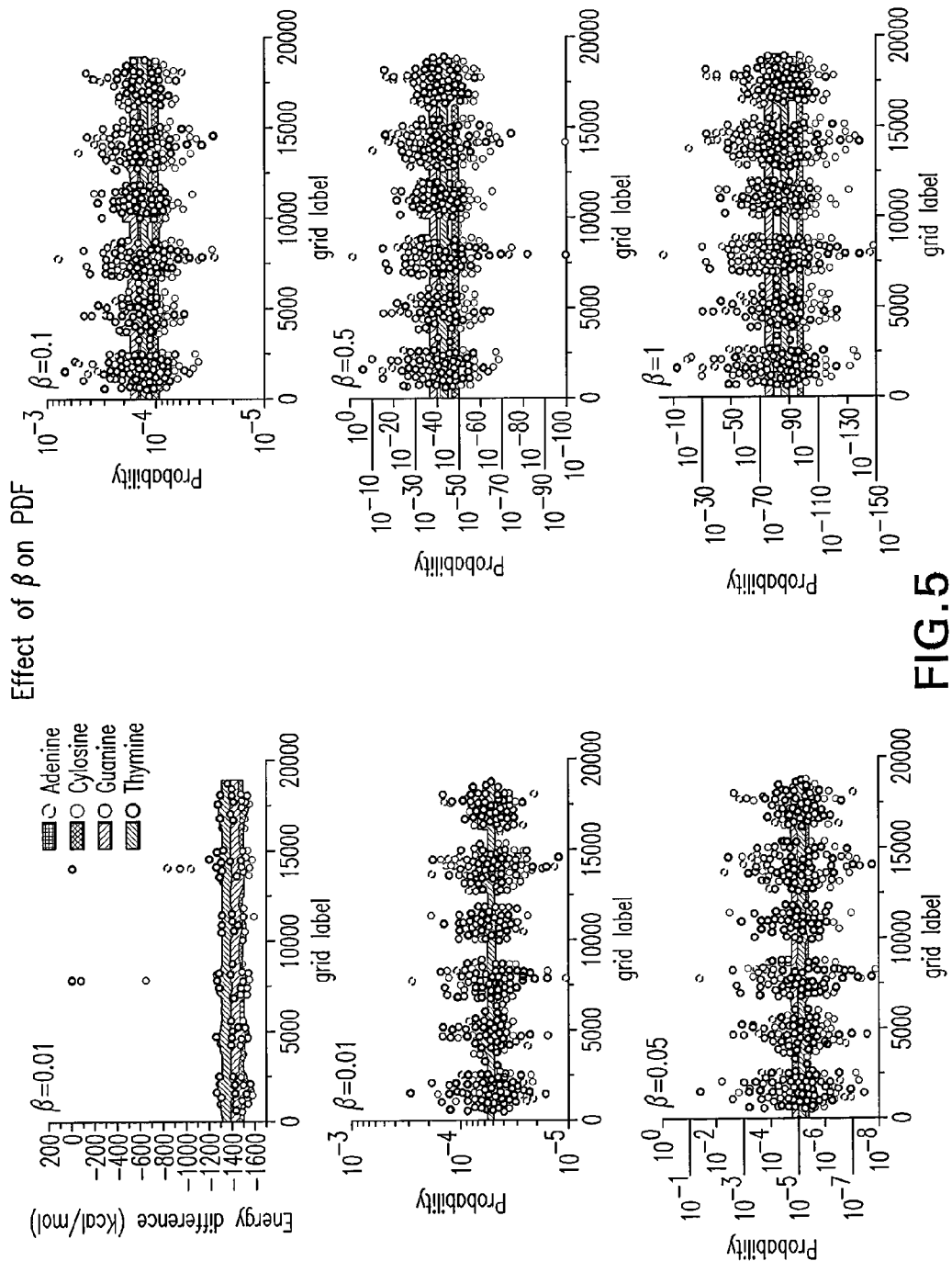
FIG. 5 is a depiction of the probability and energy differences of various nucleotides as they bind to different surfaces of a target molecule.

The probability distributions of four types of the first nucleotide at all grid points were calculated under various considerations for the Lagrange multipliers. The results are shown in FIG. 5. The top left panel shows an example of a shifted total energy versus grid label for the case of β=0.01. Note that the grid label denotes a specific location and orientation. All probability distributions have similar patterns with six wave packet-liked shapes around the same grid labels. These results suggest six groups of potential binding sites surrounding thrombin protein for the first nucleotide. As shown in the figure, there are some grid points that have the same energy. They are from the overlapping grids, which are not excluded during the creation of the grid space because they do not influence the final result. The relative entropy for the probability distribution of each type and a uniform distribution then is calculated using Eq. (3). For β=0.01, the relative entropy values in increased order are: −2.4393 for G, −2.2248 for C, −2.1162 for T and −1.829 for A. This order is retained for all Lagrange multipliers considered and therefore the entropic criterion indicates that the type of the preferred seed is guanine and the preferred location and orientation is the one with the maximum probability. It follows that the first identified nucleotide is G.

Figure 6:
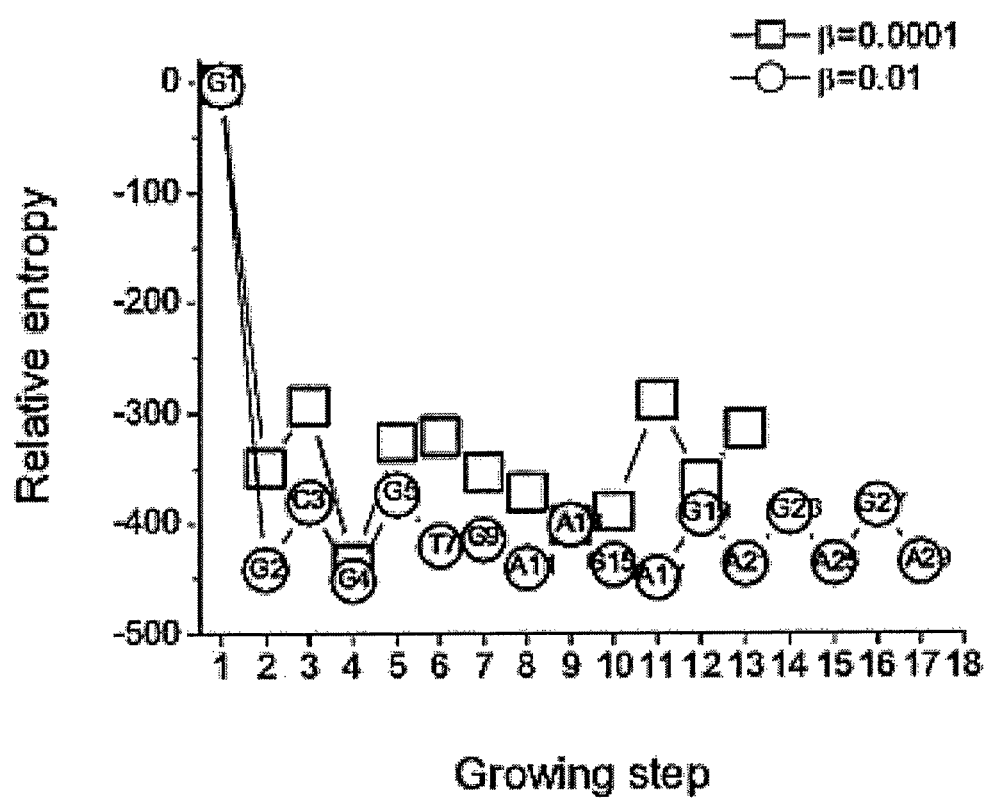
FIG. 6 is a graph depicting relative entropy for a particular aptamer as it undergoes the growth stage of the inventive method.

Having determined the first nucleotide, the rest of the sequence was determined in a similar fashion until the stopping criterion is met as shown in FIG. 6. It shows the relative entropy value at each step of the growth process marked by open symbols with the consideration of two values of the Lagrange multiplier β. For β=0.01. The preferred nucleotide type is also listed inside the symbol. Note that the odd numbers of growth steps, except for the first step, refer to the nucleotide to be connected to the 3' end of the previous one and the even numbers are for the other side. The curve indicates that relative entropy fluctuates around −400 after the 11$^{th}$ step for β=0.01 and around −350 after the 13$^{th}$ step for β=0.0001. Both calculations suggest that the nucleotides added after either the 11$^{th}$ or 13$^{th}$ step does not enhance the interactions between the nucleotide fragment and thrombin. Therefore, one can conclude that the 8-mer DNA sequence 5'-GGGCGTGA-3' is the preferred ME-aptamer most likely to bind to thrombin.

Example 2

Comparison of ME-Determined Aptamer to SELEX-Determined Aptamer

The primary structure of a known (SELEX-determined) thrombin aptamer has been identified as GGTTGGTGTGGT-TGG (SEQ ID NO. 1). See U.S. Pat. No. 5,476,766 to Gold. Positions 3 and 7-9 (underscored below) of the thrombin aptamer are known to tolerate variation while maintaining acceptable binding to thrombin. This known aptamer serves as a comparative benchmark.

(ME)      G G G C G T G A (SELEX)   G G T̲ T G G T̲ G̲ T̲ G G T T G G SEQ ID NO. 1

A 1.4 ns MD simulation was conducted to equilibrate the ME and SELEX aptamers separately. Two analyses, the potential energy of ME and SELEX aptamer-thrombin complexes and the root-mean-square-deviation between the structures during simulation and the reference, indicate that both are likely to be equilibrated.

In the first set of in silico experiments, three different DNA sequences were considered to examine specificity, namely whether the ME prediction is preferred over all other possibilities. They had exactly the same composition as in the ME prediction except the 3' end nucleotide A of the ME predicted sequence was replaced by the other three nucleotides, respectively, and one that was generated randomly. If the ME prediction is found to be preferred over these three, one can expect there will be no other with higher specificity than the ME prediction. Therefore, there was no need to examine other sequences. The three DNA sequences are denoted by "R_c", "R_g" and "R_t" and the random sequence is denoted by "random". All of them are given the same structure predicted from the 3D-DART web serve. Since the 3D-DART web server actually predicts a double strand DNA tertiary structure based sequence, a single strand was manually extracted and equilibrated it using MD simulation for 1 ns under explicit water conditions. Finally, the final structure was manually placed at the location of the center of mass of the ME prediction to create an aptamer-thrombin complex for simulations.

The mean binding free energy estimates based on the MM PBSA/GBSA calculations for the five sequences, ME_dart, R_c, R_g, R_t, and the complete random sequence, are shown in FIG. 7A. Although the large standard deviations in all cases show the structural data collected from MD simulations are not yet sufficient for statistical analysis, the trends of the mean binding free energies still highlight the differences among these five cases. For ME_dart, R_g and R_t, both MM-PBSA and MM_GBSA estimates show the binding free energy gradually decreases when the simulation length is increased. Although the MM-PBSA calculation for R_t seems to compete with ME_dart, MM-GBSA shows that ME_dart outperforms other sequences. For R_c and the random sequence, both MM-PBSA/GBSA show that ME_dart has the lowest binding free energy. Although the R_c, R_g and R_t sequences differ from the ME_dart by only one nucleotide, the binding free energy estimate shows that ME_dart is preferred over these sequences. These results support our global maximum entropy argument. Furthermore, this also suggests that the ME prediction possesses high binding specificity.

Estimates of the binding affinity of the ME and SELEX aptamers using MM-PBSA/GBSA free energy calculations were also analyzed. The binding free energy estimates for four various initial conditions based on the structural data collected from five MD simulations with various temporal lengths were calculated and are shown in FIG. 7B. Although MM-GBSA shows ME_final has the lowest binding free energy, MM-PBSA still suggests it is compatible with Exp_final. For Exp_dart and ME_dart, it again shows both have similar binding free energies. This also suggests that the sequence difference between Exp_dart and ME_dart has only a minor influence on binding affinity. Therefore there must be some common nucleotides present in both sequences which play important roles in the interactions. As revealed in the interaction analysis, the domain TGA for the ME aptamer and TGT for the SELEX aptamer are likely those common nucleotides.

Example 3

Phosphatidylserine Aptamer—Determined of Predicted Aptamers

Phosphatidylserine is a phospholipid that is typically restricted to the cytoplasm of the cell. During apoptosis this phospholipid is exposed to the surface of the cell. Detection of phosphatidyserine is therefore considered to be an early indication of cellular apoptosis. Only two proteins, Annexin V and Mfge8, are known to detect phosphatidyserine but specificity and availability issues remain unsolved.

The molecular model of PS was manually constructed using the MOLDEN program. The resulting structure was then minimized with the GAMESS-US program using the AM1 semi-empirical method (step 102)

To design aptamers for PS, the total energy of the PS and nucleotide fragments was utilized as input information required for the design. Since apoptosis induced PS externalization at the membrane level of the cell is of interest, only the head group of PS was considered for the design since the lipid portion of the molecule remains embedded in the cell's lipid membrane. Two top-ranked sequences, 5'-AAAAGA-3' (PS-aptamer I) and AAAGAC (PS-aptamer II), were selected for experimental assays and in silico experiments intended as validation of the design method.

```
PS-aptamer I        A A A A G A

PS-aptamer II       A A A G A C
```

Example 4

PS Aptamer Study

Two liposomes were prepared for studying binding affinity and specificity. One uses DPPC and DPPS at a 10:1 DPPC/DPPS molar ratio and the second one uses DPPC alone. In both cases cholesterol exists at the DPPC/cholesterol molar ratio of 2:1. The latter served as a control without PS available for binding. Chloroform from lipid/cholesterol stock in chloroform was evaporated using a stream of nitrogen or argon. The dried chloroform-free lipids/cholesterol mixture was dissolved in HEPES buffer and 1 mL of each solution was transferred to an eppendorf tube. An appropriate amount of fluorescent labeled computationally-derived nucleotide sequence (aptamer) was then added from stock of DNA in 1× Tris/EDTA (TE) buffer. The lipid/aptamer mixture was then incubated for 40 minutes in the dark. The eppendorf tubes were centrifuged to pellet lipid and bound aptamer. Supernatants (buffer and unbound aptamer) were then removed. One mL HEPES buffer was added into each eppendorf tube, resuspended the lipid and centrifuged them again to pellet lipid and bound aptamer and the supernatants were again removed. This process was repeated three times to effectively remove unbound aptamer. One mL HEPES buffer was added into each eppendorf tube containing bound aptamer/lipids. 100 µL from this final solution was loaded into each of the 96 wells on the fluorescence plate to measure fluorescence of the samples. PC software version V1.30 R4 was used. Excitation filter was at 485 nm and emission filter at 520 nm.

Both sequences containing fluorescence tags (6FAM is on the 3' end of the DNA sequence) were obtained from Integrated DNA Technologies, Commercial Park, Coralville Iowa, USA. 96 well assay plates for fluorescence assays using FLUOstar OPTIMA (BMG Labtech GmbH, Offenburg, Germany) were from Corning Inc., New York, USA. Two lipids, 1,2-dipalmitoyl-sn-glycero-3-phosphatidylcholine (DPPC) and 1,2-dipalmitoyl-sn-glycero-3-phospho-L-serine (sodium salt) (DPPS) in chloroform stock and cholesterol (powder) were obtained from Avanti Polar Lipids (Alabaster, Ala., USA). They were used without further purification.

In order to provide theoretical insights to the binding properties of two ME aptamers, four 5 ns MD simulations were conducted with various initial structures. For the binding affinity, the complex composed of PS and two ME aptamers was used as initial structures. For the binding selectivity, the complex composed of PC and two ME aptamers was used as initial structures. The interactions between two ME aptamers and either PS or PC during the MD simulations were then analyzed using NUCPLOT to elucidate the resultant binding properties.

Figure 8:
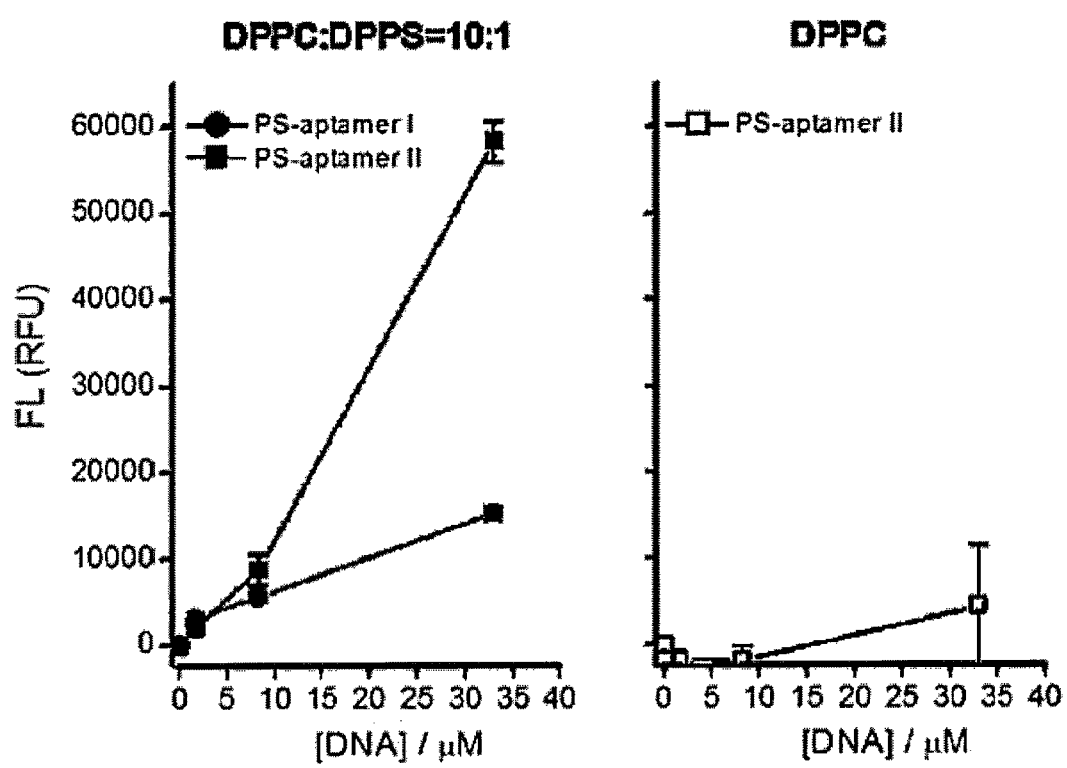
FIG. 8 illustrates the relative fluorescence of two aptamers with different liposome-bound PS targets.

FIG. 8 indicates the fluorescence level from bound DNA aptamers using various concentrations of DNA aptamers with the two types of liposomes (the right panel shows the results in DPPC alone and the left for the results in DPPC+DPPS). Two specific features are revealed. First, both DNA aptamers bind with lipid liposomes. The low fluorescent level shown in the right part of the figure indicates that PS-aptamer II binds either poorly or not at all with DPPC. On the contrary, the left panel shows a relatively high fluorescent level while DPPS is present. It suggests that both DNA aptamers bind specifically with DPPS. This indicates that the binding of the aptamers is specific to the lipid containing the serine head group. Second, although both DNA aptamers bind with DPPS, the results show PS-aptamer II has a higher fluorescence level than PS-aptamer I when the concentrations of DNA aptamers are increased beyond 0.165 nmol. This suggests that PS-aptamer II has relatively better or stronger binding affinity than PS-aptamer I.

Figure 9A:
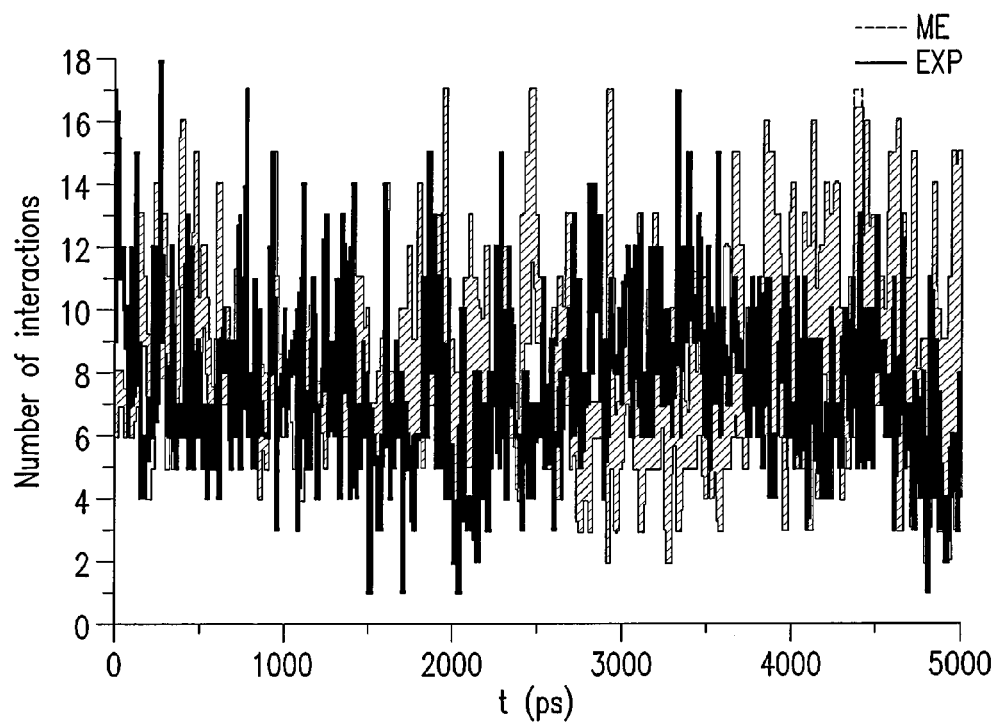
FIG. 9A shows hydrogen-bond interactions and FIG. 9B shows non-bond interactions for a particular PS-aptamer interaction.
Figure 9B:
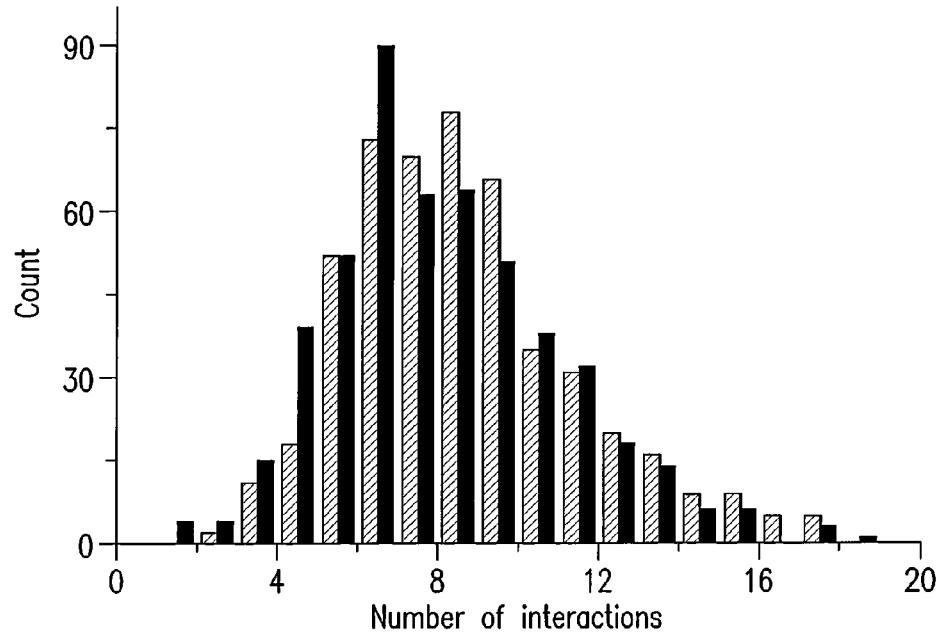

Based on in silico experiments, FIGS. 9A and 9B shows that two types of interactions, hydrogen bond (H-bond) in the upper panel (FIG. 9A) and non-bonded contacts in the lower panel (FIG. 9B). Both results were identified in the four 5 ns MD simulations. The figure indicates that there are more hydrogen bonds constantly formed between PS and PS-aptamer II than between PS and PS-aptamer I after the 4$^{th}$ ns. Even though there are some non-bonded interactions formed between PS and PS-aptamer I, PS-aptamer II is still considered to have the stronger binding affinity due to the hydrogen bond which provides a strong and direct interaction. No hydrogen bonds are observed between either PS-aptamer I or II and PC. This suggests that both ME aptamers have stronger interactions with PS than with PC suggesting some specificity in the binding of ME aptamers to PS.

While the invention has been described with reference to preferred embodiments, it will be understood by those skilled in the art that various changes may be made and equivalents may be substituted for elements thereof to adapt to particular situations without departing from the scope of the invention. Therefore, it is intended that the invention not be limited to the particular embodiments disclosed as the best mode contemplated for carrying out this invention, but that the invention will include all embodiments falling within the scope and spirit of the appended claims.

What is claimed is:

1. A method for determining an aptamer sequence comprising the steps of:
   providing a structure of a protein to a computer;
   individually modeling, with the computer, the entropic probability distribution of four individual potential first nucleotides to the protein and identifying a binding site for each of the four nucleotides;
   comparing the individual entropic probability distribution of each of the nucleotide-binding site pairings, with the computer, and selecting the pairing that has the most favorable entropic probability distribution for binding, thereby identifying a first nucleotide and its corresponding first binding site;
   individually modeling the entropic probability distribution of a plurality of different first oligonucleotides to the first binding site, with the computer, the first oligonucleotides each consisting of the first nucleotide plus one potential second nucleotide and thereafter selecting the first oligonucleotide that has the most favorable entropic probability distribution for binding, thereby identifying a second nucleotide; and
   individually modeling the entropic probability distribution of a plurality of different second oligonucleotides to the first binding site, with the computer, the second oligonucleotides consisting of the first nucleotide plus the second nucleotide disposed adjacent the first, plus one potential third nucleotide and thereafter selecting the second oligonucleotide that has the most favorable entropic probability distribution for binding, thereby identifying a third nucleotide.

2. The method as recited in claim 1, wherein the first, second and third nucleotides are independently selected from the group consisting of adenine, guanine, cytosine and thymine.

3. The method as recited in claim 1, wherein the first, second and third nucleotides are independently selected from the group consisting of adenine, uracil, guanine and cytosine.

4. The method as recited in claim 1, further comprising the step of synthesizing an aptamer that consists of the selected second oligonucleotide.

5. The method as recited in claim 1, wherein the step of modeling the entropic probability distribution of a plurality of different first oligonucleotides further includes selecting the first oligonucleotide that has the second most favorable entropic probability distribution for binding, thereby identifying an alternative second nucleotide.

6. The method as recited in claim 5, further comprising the step of identifying a plurality of alternative aptamers that are rank ordered by their entropic probability distribution for binding to the protein.

* * * * *

SEQUENCE LISTING

```
<160> NUMBER OF SEQ ID NOS: 1

<210> SEQ ID NO 1
<211> LENGTH: 15
<212> TYPE: DNA
<213> ORGANISM: Artificial Sequence
<220> FEATURE:
<223> OTHER INFORMATION: Totally synthetic DNA ligand to thrombin

<400> SEQUENCE: 1
ggttggtgtg gttgg                                                    15
```